United States Patent [19]
De Angelis et al.

[11] Patent Number: 5,400,643
[45] Date of Patent: Mar. 28, 1995

[54] GAS SENSOR BASED ON SEMICONDUCTOR OXIDE, FOR GASEOUS HYDROCARBON DETERMINATION

[75] Inventors: Lucio De Angelis, Rome; Roberto Riva, Milan; Luciano Occhio, Soncino, all of Italy

[73] Assignees: Eniricerche S.p.A.; SNAM S.p.A., both of Milan, Italy

[21] Appl. No.: 168,232

[22] Filed: Dec. 17, 1993

[30] Foreign Application Priority Data

Dec. 23, 1992 [IT] Italy .................. MI92A2939

[51] Int. Cl.⁶ .................. G01N 27/12
[52] U.S. Cl. .................. 73/31.06; 340/634; 422/98
[58] Field of Search .................. 73/31.06, 31.05; 340/632, 634; 422/98

[56] References Cited

U.S. PATENT DOCUMENTS

| | | | |
|---|---|---|---|
| 4,443,791 | 4/1984 | Risgin et al. | 73/31.06 X |
| 4,453,397 | 6/1984 | Ohta et al. | 73/31.05 X |
| 4,490,715 | 12/1984 | Kusanagi et al. | 73/31.05 X |
| 4,840,913 | 6/1989 | Logothetis et al. | |
| 5,104,513 | 4/1992 | Lee et al. | 73/31.05 X |

FOREIGN PATENT DOCUMENTS

| | | | |
|---|---|---|---|
| 0444753 | 9/1991 | European Pat. Off. | |
| 3519435 | 12/1986 | Germany | |
| 29935 | 2/1982 | Japan | 73/31.05 |
| 279149 | 11/1988 | Japan | 73/31.05 |
| 86550 | 3/1992 | Japan | 73/31.05 |

Primary Examiner—Hezron E. Williams
Assistant Examiner—Joseph W. Roskos
Attorney, Agent, or Firm—Oblon, Spivak, McClelland, Maier, & Neustadt

[57] ABSTRACT

A sensor device for gaseous hydrocarbons includes two semiconductor oxide-based sensitive elements, one of which is a sensitive reference element and the other a sensitive measuring element, this measuring element being covered with a layer of electrically insulating porous material containing a dispersed noble metal. The two sensitive elements are formed by silk-screen processes, are connected to an electronic signal comparison system, and are maintained at different temperatures when in operation. The sensor has improved selectivity in determining gaseous hydrocarbons, in particular methane, even if high concentrations of interfering gases such as ethanol are present.

9 Claims, 7 Drawing Sheets

GAS SENSOR BASED ON SEMICONDUCTOR OXIDE, FOR GASEOUS HYDROCARBON DETERMINATION

BACKGROUND OF THE INVENTION

1. Field of the Invention

This invention relates to a sensor device for the selective determination of gaseous hydrocarbons.

2. Description of the Related Art

The development of easily read instruments, including portable instruments, for determining methane or other hydrocarbons is closely linked to the development of low-cost sensors of high sensitivity. From the time it was discovered that the adsorption of a gas on the surface of semiconductor oxides produces a variation in the electrical resistance of the material and that this effect is reversible, it has been attempted to utilize these properties for forming simple low-cost gas sensors. Sensors of this type are described for example in Chemical Sensor Technology, Ed. Tetsuro Seijama, Elsevier 1988. The perfection of this type of device has been rather lengthy and difficult because a sensor based on semiconductor oxide is intrinsically non-selective. In this respect it is sensitive not towards a single species but towards all those species which interact with its surface. Other problems concern stability and reproducibility, which together with selectivity represent the greatest problems to be solved before the use of such low-cost devices can become widespread.

Stability and reproducibility can be improved by improving the method of construction of the sensitive element, whereas selectivity can be improved by finding catalysts effective for a certain type of gas, by depositing suitable filters on the surface of the sensitive element and by forming an array. An array, as described for example in U.S. Pat. Nos. 4,457,161 and 4,542,640, consists of a plurality of sensors, each of which reacts differently towards the interaction with the gases contained in a determined mixture, to hence produce a different response. By processing these responses, methane or other gaseous hydrocarbons can be distinguished from other species (such as ethanol) which if only a single sensitive element were used could interfere with the measurement.

U.S. Pat. No. 4,911,892 and GB patent 2,002,907 apply the idea of using a single sensitive element but provided with a "filter" consisting of a material which favours combustion of the interfering gases, hence improving the sensitivity and selectivity of the sensor towards the species to be determined. The major drawback of this construction is that high quantities of interfering gas can cause false alarms.

European patent application publication No. 444,753 describes a hydrocarbon sensor device consisting of two sensitive elements based on amorphous semiconductor oxide, one for measurement and the other as reference, which are maintained at different operating temperatures. This method achieves discrimination between methane and interfering gases without the need for complicated processing of the signals and in particular without the need to use an array, however the sensor selectivity is unsatisfactory when the interfering gas concentration is very high.

It has now been found, according to the present invention, that by combining a sensitive measuring element, protected in the manner described hereinafter, with a sensitive reference element within a sensor based on semiconductor oxide of crystalline nature, the sensor exhibits high selectivity in determining gaseous hydrocarbons, said selectivity also being exhibited if high interfering gas concentrations are present. It therefore becomes possible to form a highly sensitive sensor in which the gaseous hydrocarbon alarm threshold, in particular for methane, is practically unaltered by the presence of interfering gases, particularly ethanol, within a wide interfering gas concentration range. The sensor device of the present invention is hence highly reliable and substantially free of the false alarm phenomena which afflict sensors of the known art.

In accordance therewith the present invention provides a semiconductor oxide-based sensor device for methane and other gaseous hydrocarbons, comprising an insulating material support carrying a heating element on one of its major surfaces, and a sensitive measuring element and a sensitive reference element on its other major surface, characterised in that:

said sensitive measuring element and said sensitive reference element are formed of crystalline tin oxide, alumina and noble metal and are in the form of thick film deposited by a silk-screen process;

said sensitive measuring element is covered with a layer of electrically insulating porous material in which a noble metal is dispersed;

said sensitive measuring and reference elements being heated by said heating element to mutually different temperatures and being operationally connected to an electronic comparator circuit able to measure the conductance which the sensitive elements assume by interaction with the gas, compare the signals emitted by the sensitive reference element and by the sensitive measuring element, and evaluate the presence and concentration of the hydrocarbon gas on the basis of said comparison of said signals.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The invention is described in detail hereinafter with reference to FIG. 1 in which a sensor device is shown schematically in front view (A), rear view (B) and side view (C).

In this figure the reference numeral 1 indicates a support, in the form of a plate of insulating material such as alumina, on the front face of which there are provided sensitive measuring and reference elements 2 and 3. Said sensitive elements 2 and 3, with a thickness typically of the order of 100 μm, are deposited by a silk-screen process from a paste containing tin oxide, alumina and a noble metal, preferably platinum or palladium.

Such a paste is conveniently prepared by suspending tin oxide powder ($SnO_2$) and alumina powder ($Al_2O_3$), with a particle size of less than 1 μm, in an inert organic solvent in a weight ratio of between 5:2 and 1:1, and adding the noble metal in the form of an organometallic precursor in a quantity such as to achieve a noble metal concentration in the final sensitive elements of at least 0.1% and up to about 3% by weight, and preferably of the order of 1% by weight. The viscosity of the paste is between 20,000 and 30,000 mPa.s, with a velocity gradient of 100 sec$^{-1}$.

A layer of electrically insulating porous material 4 containing a dispersed noble metal is deposited on the sensitive measuring element 2 to a thickness typically of the order of 20–30 μm. The electrically insulating material can be for example alumina and the noble metal palladium or platinum, these being present in a quantity of at least 0.1% and up to about 3% by weight, and preferably of the order of 1% by weight.

Both the sensitive elements 2 and 3 and the layer of electrically insulating material 4 can be prepared by a process comprising the following successive steps:
a) silk-screen printing: deposition of the film by a silk-screen process using commercially available apparatus specific for the purpose;
b) levelling: as the silk-screen film comprises a network of lines on its surface due to the impression of the frame screen, this defect is eliminated by leaving the sample in air at ambient temperature for a few minutes;
c) drying: this is done in an oven at a temperature of between 90° C. and 200° C.; during this step the more volatile substances of the silk-screen paste are eliminated with a weight loss of about 40% of the total, and the film acquires a certain consistency;
d) high-temperature firing: the firing of the silk-screen film is a step in which the solvents and organic binders are eliminated combustion; the firing is done in a kiln in air at a temperature of between 600° C. and 1200° C.

The process can be conducted by repeating steps a) to d) several times, or by repeating steps a) to c) several times and effecting only one final firing d).

Figure 1A:
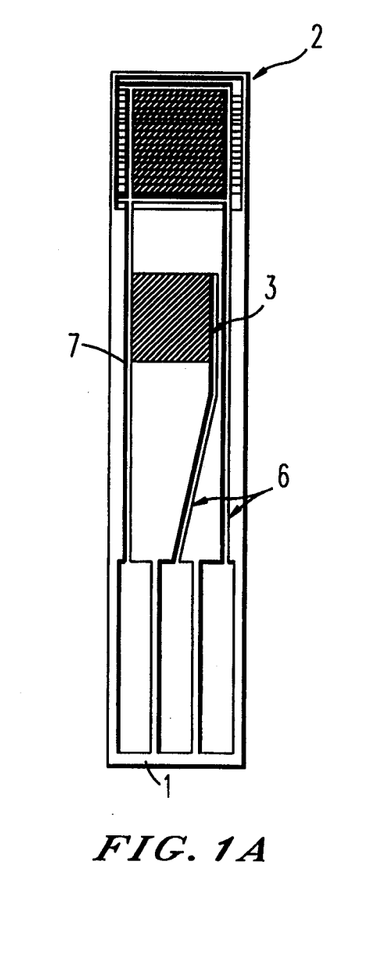
FIGS. 1A–1C illustrate a front view, rear view, and side view of a sensor device according to a first embodiment of the present invention.
Figure 1B:
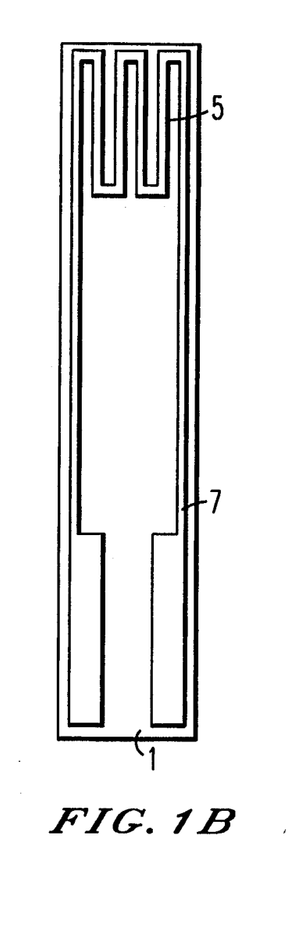
Figure 1C:
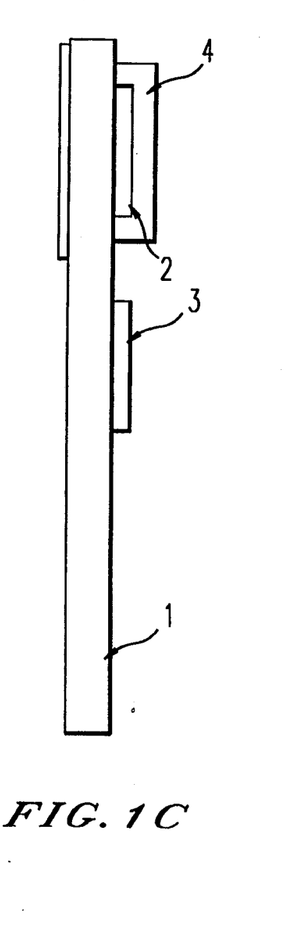
Figure 2A:
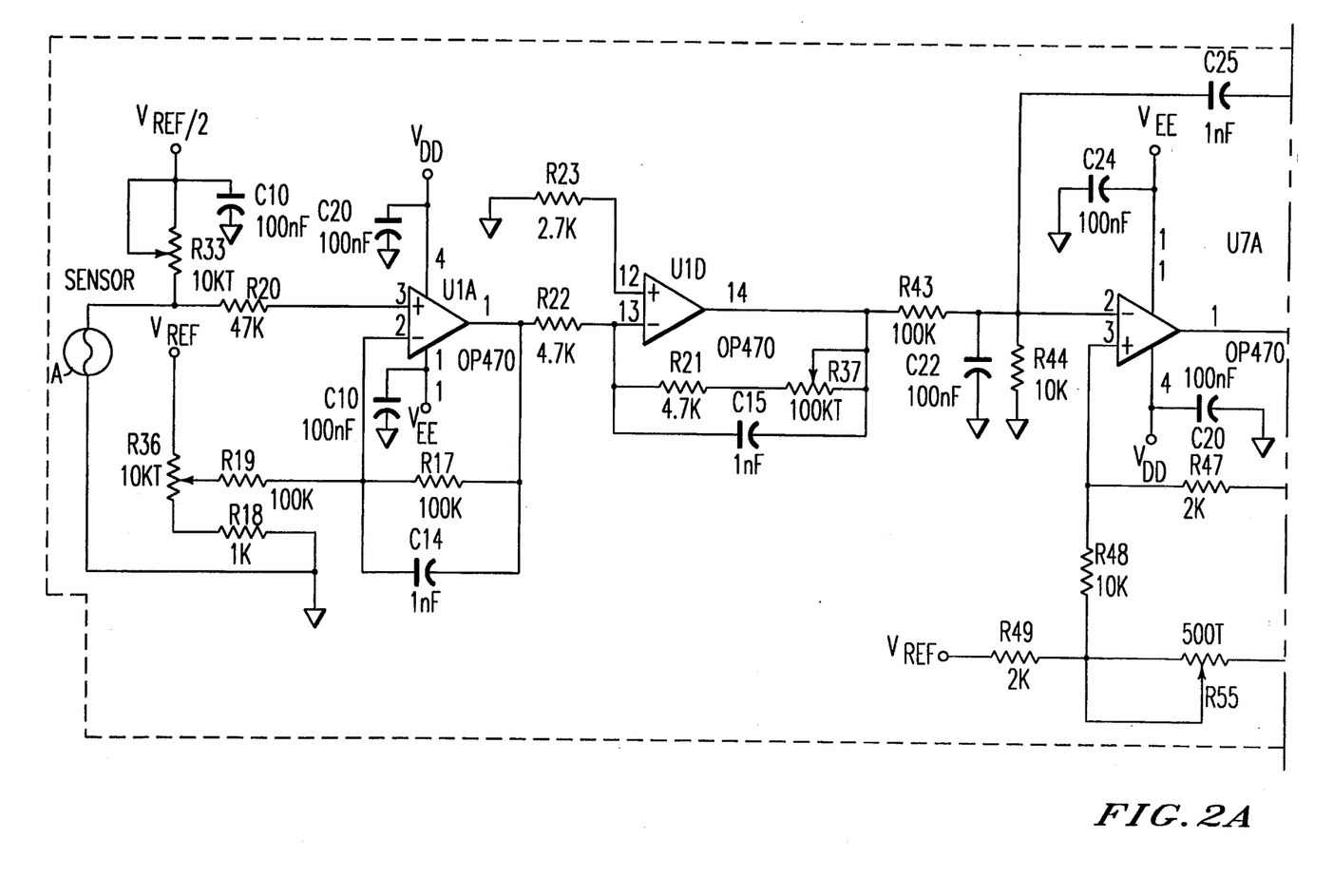
FIG. 2A–D illustrates an electronic comparator for controlling an alarm system according to the present invention.
Figure 2B:
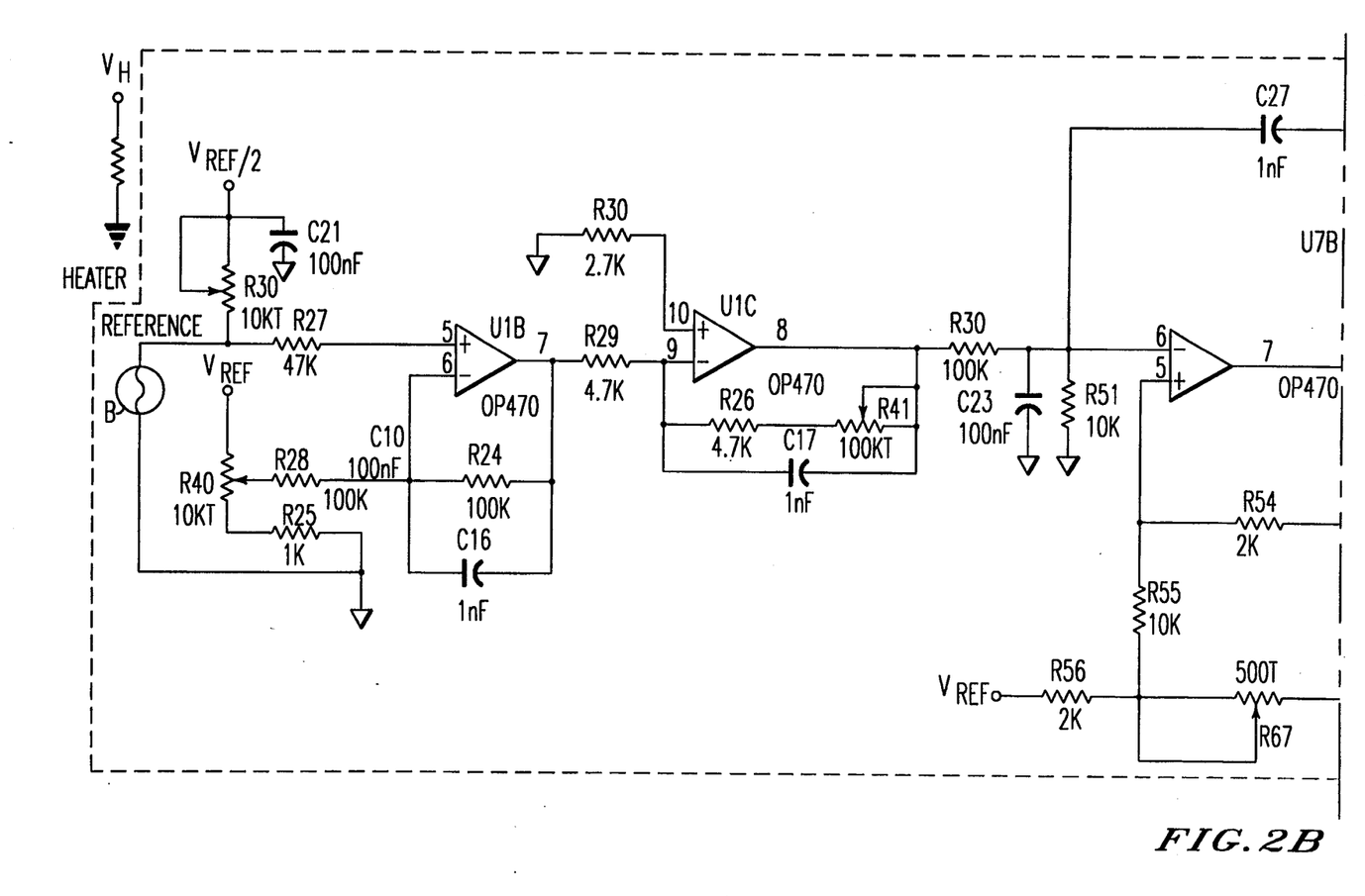
Figure 2C:
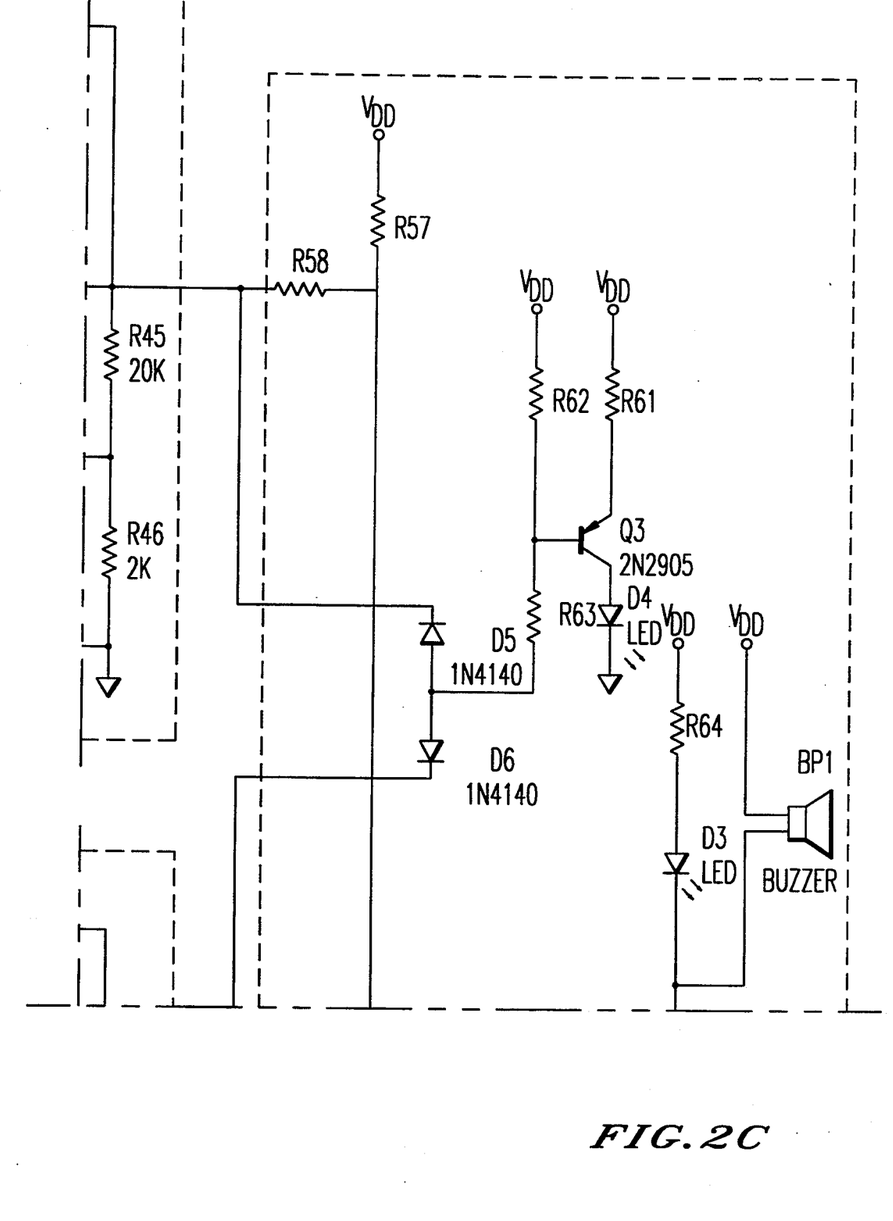
Figure 2D:
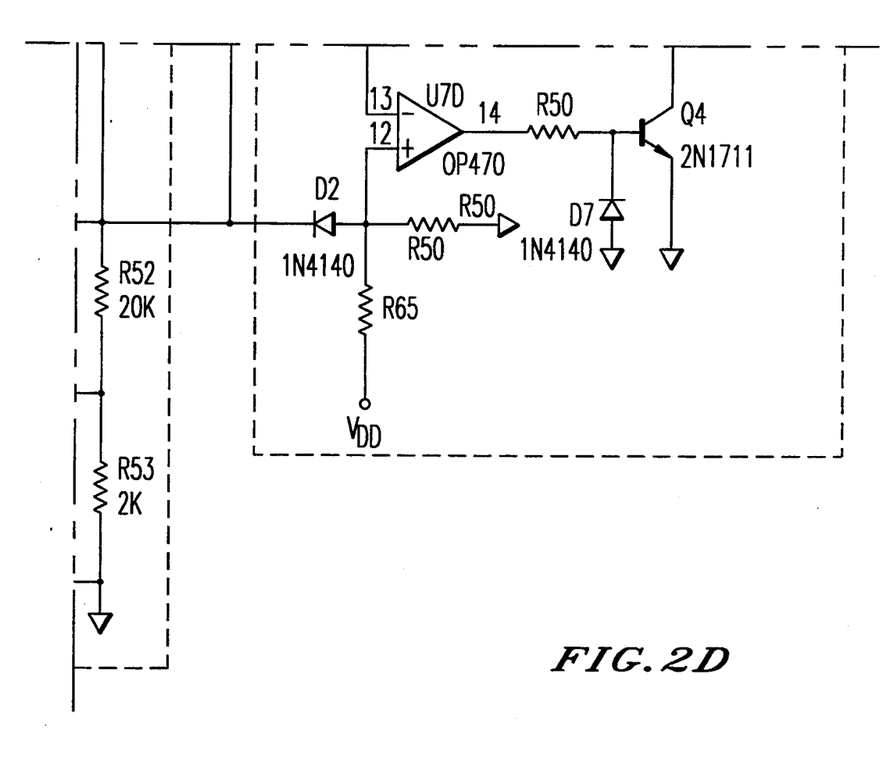

With reference to FIG. 1, the heating element 5 is deposited on the rear face of the support 1 with a geometry such as to form a temperature gradient on the front face which maintains the sensitive elements 2 and 3 at different operating temperatures. Specifically, the sensitive measuring element is maintained at a temperature of between 400° and 550° C. and the reference element at a temperature of between 200° and 400° C., with a temperature difference between the two elements of at least 50° C.

FIG. 1 also shows the electrical contacts 6 of the sensitive elements and the electrical contacts 7 of the heating element, these being formed with commercial pastes based on platinum or gold.

The various other constituent elements of the sensor device are conveniently deposited by a silk-screen process from the relative pastes, via the silk-screen printing, levelling, drying and firing steps similar to the sensitive measuring and reference elements and the layer of electrically insulating material, as heretofore described. The order of deposition depends essentially on the final firing temperature, in the sense that those elements requiring the highest firing temperatures are deposited first. On the basis of the aforegoing, in constructing the sensor device of the present invention the procedure is as follows: the heating element is firstly silk-screen printed on the support, it is then protected against external agents, after which the terminals of the heating element are printed; this is then followed by the electrodes of the sensitive measuring and reference elements and their terminals; and finally by the sensitive measuring and reference elements themselves.

Figure 3A:
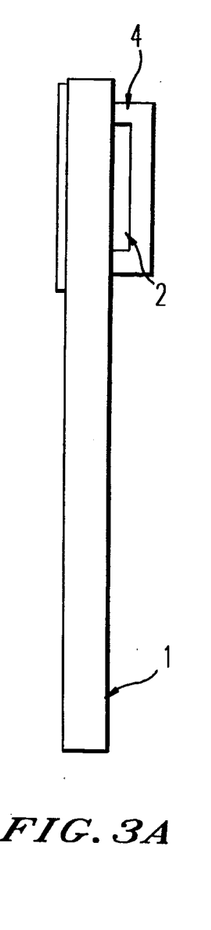
FIG. 3A–3F illustrates front views, rear views, and side views of a second embodiment of the present invention wherein sensitive reference and measuring elements are deposited on two different supports each provided with a heating element.
Figure 3B:
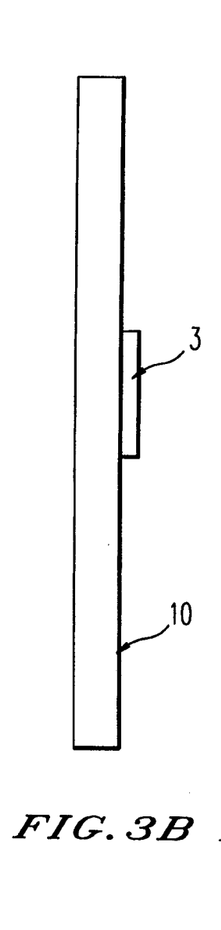
Figures 3C, 3D:
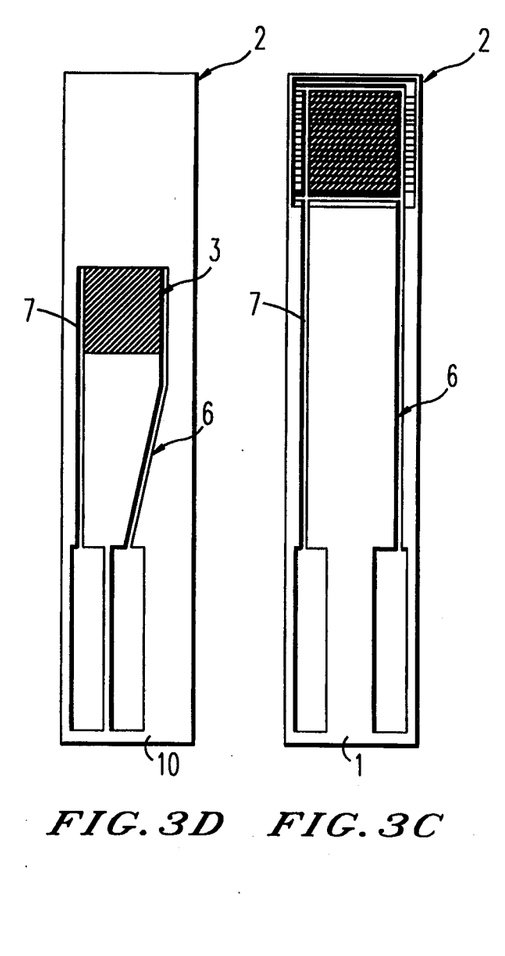
Figure 3E:
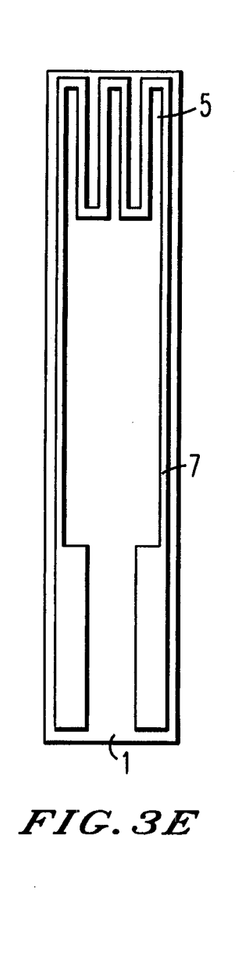
Figure 3F:
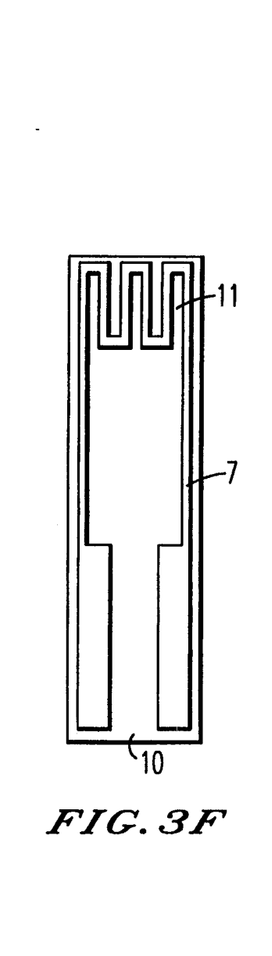

According to a further embodiment the sensitive reference and measuring elements are deposited on two different supports each provided with a heating element. This embodiment is illustrated in FIG. 3, where FIGS. 3A, 3C and 3E show a front view, a rear view, and side view of the sensitive measuring element 2 deposited on a single support 1 provided with the heating element 5. Likewise, FIGS. 3B, 3D, and 3F show a front view, a rear view, and side view of the sensitive reference element 3 deposited on a different support 10 provided with the heating element 11.

Figure 4:
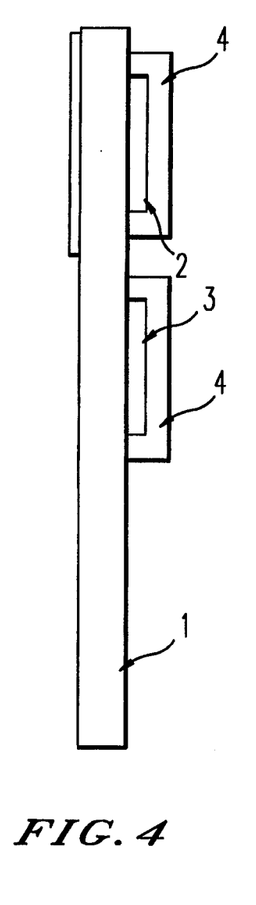
FIG. 4 illustrates a third embodiment of the present invention wherein a layer of electrically insulating material containing dispersed noble metal is deposited on the sensitive reference element as well as the sensitive measuring element.

According to a further embodiment the layer of electrically insulating material containing dispersed noble metal is also deposited on the sensitive reference element, in a manner similar to the sensitive measuring element. This embodiment is illustrated in FIG. 4, where it is shown that a layer of electrically insulating porous material 4 containing a dispersed noble metal is deposited on the sensitive reference element 3 as well as the sensitive measuring element 2.

As already stated, the sensitive measuring and reference elements are operationally connected to an electronic comparator circuit able to measure the conductance which the sensitive elements assume by interaction with the gas, compare the signals emitted by the sensitive reference element and by the sensitive measuring element, and evaluate the presence and concentration of the hydrocarbon gas on the basis of said signal comparison.

FIG. 2 of the drawings shows an electronic comparator scheme usable for controlling the alarm system and comprising a first amplifier D for amplifying the signals generated by the sensitive measuring element, and a second amplifier F for amplifying the signals generated by the sensitive reference element, said signals being processed and compared in the section E to emit an acoustic and light signal if methane or another hydrocarbon gas is present in a concentration exceeding the predetermined threshold value. If the reference element signals the presence of interfering gases, in particular ethanol in a concentration of about 2000 ppm, a light signal is emitted and the alarm signal for methane inhibited.

In this manner a highly sensitive and reliable sensor device is obtained. In particular in said sensor the gaseous hydrocarbon alarm threshold is hardly changed by the presence of interfering gases within a wide interfering gas concentration range. For example the methane alarm threshold, which typically can be fixed between 0.2 and 1.0%, is practically unchanged by the presence of ethanol, a gas normally present in domestic kitchens, up to an ethanol concentration of about 2000 ppm. Consequently the sensor device of the present invention is highly reliable as it substantially eliminates false alarms under normal conditions of use.

The following examples are provided for a better understanding of the invention, but must not be considered as limitative thereof.

EXAMPLE 1

The heating element is deposited by a silk-screen process on one face of a support consisting of a standard alumina plate (side dimensions 5×5 cm, thickness 0.6 mm).

For the deposition a commercial apparatus is used having frames with a 325 mesh steel screen in which the apertures are orientated at 45° to the line of advancement of the doctor blade. The doctor blade speed is 15 cm/sec and the pressure 4 kg. The resistive paste is platinum-based ESL 5545 commercial silk-screen paste.

After levelling for 10 minutes the plate is dried in an oven for 10 minutes at 125° C. High-temperature firing is conducted in a belt kiln for 10 minutes at 970° C. and for a further 10 minutes at 1200° C. The heating element obtained in this manner is of hairpin-coil shape with a thickness of 10-12 μm and a resistance of about 10 ohms.

The heating element is protected and the terminals formed by the same procedure, using a paste such as Heraeus IP9117-S for the protective layer and Du Pont 4596 for the terminals. The comb-shaped gold or platinum contacts, the weldable tin pads at the end of the contacts and the gas-sensitive part are then deposited in succession on the opposite face of the alumina plate. The contacts are of comb shape to provide a high surface of contact with the sensitive part. They are formed using the same procedure and same paste as used for the the heating element contacts. Weldable tin pads are deposited at their ends by the silk-screen process, as for the heating element.

The gas-sensitive part is deposited by the silk-screen process using a paste of the following composition:
CERAC 99.9% $SnO_2$, particle size less than 1 μm, 45.5%;
Baikowski 99.9% $Al_2O_3$, particle size less than 1 μm, 18.2%;
Heraeus 7811/L solution containing 8% platinum, 2.8%;
organic vehicle consisting of Fluka RP alpha terpineol and Fluka RP ethylcellulose 7 mPa.s in the ratio 92:8, 27.4%; and
butylcarbonyl acetate (BCA), 6.1%.

The percentages are on the total weight of the prepared paste. The films, which form the sensitive measuring and reference elements, are deposited by effecting the silk-screen printing, levelling and drying steps four times.

An electrically insulating porous material composed of $Al_2O_3$ with a particle size of less than 1 μm and containing 1 wt % of platinum is then deposited on the sensitive measuring element. The purpose of this layer is to improve the selectivity of the measuring element in that any interfering gases such as ethanol react preferentially with it. The firing step is then conducted once only at 870° C.

The sensitive element film thickness is of the order of 100 μm and the thickness of the electrically insulating porous material layer is of the order of 20 μm.

EXAMPLE 2

Using the procedure of Example 1 a sensor device is constructed consisting of two sensitive elements connected to an electronic control unit enabling the operating temperature of the two elements to be continuously controlled.

Again using the procedure of Example 1 a further sensor device is constructed for comparison purposes, but without the layer of electrically insulating porous material on the sensitive measuring element.

As the control unit enables the two sensitive elements of the device to be maintained at different temperatures, one of them can be used to measure the methane concentration by maintaining it at a temperature of 500° C. and the other can be used for measuring the concentration of ethanol as interfering gas by maintaining it at 300° C.

Table 1 shows the sensitivity values, expressed as $(R_{air}-R_{gas})/R_{gas}$, of the sensitive element maintained at high temperature (500° C). It can be seen that the sensitivity at 10,000 ppm of methane in air is about 10, whereas the sensitivity at 2000 ppm of ethanol is about 3. Hence this sensitive element can be used for measuring methane concentration.

The element maintained at low temperature (300° C.) has high sensitivity at 2000 ppm of ethanol, with $(R_{air}-R_{gas})/R_{gas}$ values exceeding 100. In contrast its sensitivity at 10,000 ppm of methane is reduced to between 3 and 6, hence this sensitive element can be used for measuring ethanol concentration. By measuring the resistance of both sensitive elements false alarms are prevented even if a very high ethanol concentration is present. In this respect, if a considerable reduction occurs in the measured resistance of the sensitive element maintained at the lower temperature, the control unit inhibits the alarm circuit connected to the methane-sensitive element.

Table 1 also shows that if a layer of electrically insulating porous material is used on the sensitive measuring element, the methane-sensitivity value remains constant at 10, whereas the sensitivity at 2000 ppm of ethanol in air falls to 0.2. It is found that the alarm threshold for methane remains unchanged even if about 2000 ppm of ethanol are present.

TABLE 1

|  |  | $(R_{air}-R_{gas})/R_{gas}$ |
|---|---|---|
| Without filter: | ethanol 2000 ppm in air | 3 |
|  | methanol 10,000 ppm in air | 10 |
| With filter: | ethanol 2000 ppm in air | 0.2 |
|  | methanol 10,000 ppm in air | 10 |

In the aforegoing table the term "filter" means the layer of electrically insulating porous material on the sensitive measuring element.

In conclusion, the alumina filter results in greater methane selectivity, whereas the reference element enables interfering gases, particularly ethanol, to be measured independently, this not being possible with a single sensitive element, the electronic control unit providing two separate signals, one from the sensitive measuring element and the other from the sensitive reference element.

We claim:
1. A semiconductor oxide-based sensor device for methane and other gaseous hydrocarbons, comprising an insulating material support carrying a heating ele- ment on one of its major surfaces, and a sensitive measuring element and a sensitive reference element on its other major surface, characterised in that:

said sensitive measuring element and said sensitive reference element are formed of crystalline tin oxide, alumina and noble metal and are in the form of thick film deposited by a silk-screen process;

said sensitive measuring element is covered with a layer of electrically insulating porous material in which a noble metal is dispersed;

said sensitive measuring and reference elements being heated by said heating element to mutually different temperatures and being operationally connected to an electronic comparator circuit able to measure the conductance which the sensitive elements assume by interaction with the gas, compare the signals emitted by the sensitive reference element and by the sensitive measuring element, and evaluate the presence and concentration of the hydrocarbon gas on the basis of said comparison of said signals.

2. A sensor device as claimed in claim 1, characterised in that said sensitive elements, with a thickness of the order of 100 μm, are deposited by a silk-screen process from a paste containing tin oxide and alumina with a particle size of less than 1 μm in a weight ratio of between 5:2 and 1:1, and a noble metal, preferably platinum or palladium, added in the form of an organometallic precursor in a quantity such as to achieve a noble metal concentration in the final sensitive elements of at least 0.1% and up to about 3% by weight, and preferably of the order of 1% by weight.

3. A sensor device as claimed in claim 1, characterised in that the layer of electrically insulating porous material deposited on the sensitive measuring element has a thickness of the order of 20–30 μm, and consists of alumina containing dispersed palladium or platinum in a quantity of at least 0.1% and up to about 3% by weight, and preferably of the order of 1% by weight.

4. A sensor device as claimed in claim 1, characterised in that the sensitive reference element is also covered with a layer of electrically insulating porous material in which a noble metal is dispersed.

5. A sensor device as claimed in claim 1, characterised in that the sensitive measuring and reference elements are deposited on two different supports, each provided with a heating element.

6. A sensor device as claimed in claim 1, characterised in that said heating element is comprised of platinum and is in the form of a hairpin coil with a thickness of 10–12 microns and a resistance of about 10 ohms.

7. A sensor device as claimed in claim 1, characterised in that the sensitive measuring element is maintained at a temperature of between 400° and 550° C. and the reference element at a temperature of between 200° and 400° C., the temperature difference between the two elements being at least 50° C.

8. A sensor device as claimed in claim 1, characterised in that the elements of the sensor are deposited on the support by the following successive steps:
  a) depositing the film by a silk-screen process,
  b) levelling the silk-screen printed film,
  c) drying the levelled film at a temperature of between 90° C. and 200° C.,
  d) firing the dried film at a temperature of between 600° C. and 1200° C.

9. A sensor device as claimed in claim 1, characterised in that the electronic comparator circuit comprises a first amplifier for amplifying the signals generated by the sensitive measuring element, a second amplifier for amplifying the signals generated by the sensitive reference element, and a section for processing and comparing said signals which is able to emit an acoustic and/or light signal if methane or another hydrocarbon gas is present in a concentration exceeding the predetermined threshold value.

* * * * *